United States Patent
Groppe

(10) Patent No.: US 9,974,784 B2
(45) Date of Patent: May 22, 2018

(54) INHIBITORS OF ACTIVIN-LIKE RECEPTOR KINASES

(71) Applicant: The Texas A & M University System, College Station, TX (US)

(72) Inventor: Jay Clemens Groppe, Lancaster, TX (US)

(73) Assignee: The Texas A&M University System, College Station, TX (US)

( * ) Notice: Subject to any disclaimer, the term of this patent is extended or adjusted under 35 U.S.C. 154(b) by 0 days. days.

(21) Appl. No.: 15/003,497

(22) Filed: Jan. 21, 2016

(65) Prior Publication Data

US 2016/0206613 A1    Jul. 21, 2016

Related U.S. Application Data

(60) Provisional application No. 62/105,955, filed on Jan. 21, 2015.

(51) Int. Cl.
| | |
|---|---|
| *A61K 31/496* | (2006.01) |
| *A61K 31/4439* | (2006.01) |
| *A61K 31/454* | (2006.01) |
| *A61K 31/4545* | (2006.01) |
| *A61K 31/473* | (2006.01) |
| *C12Q 1/48* | (2006.01) |

(52) U.S. Cl.
CPC ........ *A61K 31/496* (2013.01); *A61K 31/4439* (2013.01); *A61K 31/454* (2013.01); *A61K 31/4545* (2013.01); *A61K 31/473* (2013.01); *C12Q 1/485* (2013.01); *G01N 2333/912* (2013.01); *G01N 2500/04* (2013.01); *G01N 2500/20* (2013.01)

(58) Field of Classification Search
CPC .............. A61K 31/496; A61K 31/4439; A61K 31/4545; A61K 31/473
USPC ...................................... 514/254.03
See application file for complete search history.

(56) References Cited

U.S. PATENT DOCUMENTS 9,085,575 B2 * 7/2015 Rabot .................. C07D 471/04

FOREIGN PATENT DOCUMENTS

WO    WO 2012140114 A1 * 10/2012 ........... C07D 471/04

* cited by examiner

*Primary Examiner* — Yevgeny Valenrod
(74) *Attorney, Agent, or Firm* — Winstead PC

(57) ABSTRACT

The claimed invention is directed to a method for screening a compound that binds to an allosteric site of ALK2, the method comprising screening for a compound that is capable of destabilizing the ALK2 protein. A further aspect of the invention is directed to a pharmaceutical composition for the treatment and/or prophylaxis of a disease in a vertebrate, said composition comprising at least one ALK receptor kinase inhibitor, and optionally a pharmaceutically acceptable carrier, adjuvant and/or diluent.

8 Claims, 11 Drawing Sheets

INHIBITORS OF ACTIVIN-LIKE RECEPTOR KINASES

CROSS-REFERENCES TO RELATED APPLICATIONS

This application claims the benefit under 35 U.S.C. § 119(e) of U.S. Provisional Patent Application No. 62/105,955 filed Jan. 21, 2015 which is incorporated herein by reference in its entirety as if fully set forth herein.

FIELD OF THE INVENTION

The present invention relates to methods for identifying inhibitors of activin-like receptor kinases, specifically ALK2 and compositions comprising the identified inhibitor compounds.

BACKGROUND OF THE INVENTION

A single mutation (Arg206His) within the kinase domain of one (ACVR1/ALK2) of the four human bone morphogenetic protein (BMP) receptors has been linked to a catastrophic disorder of secondary (heterotopic) bone formation known to mankind. As a result of the substitution with histidine, all children presenting with features of classic FOP (Fibrodysplasia Ossificans Progressiva) eventually become encased in, and their movement blocked by, a second heterotopic skeleton. The disorder has long been associated with dysregulation of BMP signaling in soft tissues (skeletal muscle, tendon, ligament, fascia) that were transformed into ribbons, sheets and plates of heterotopic bone via an endochondral process. In addition to the common R206H mutation linked to the classic form of FOP (71/88 patients), other dysregulating mutations have been identified in ACVR1/ALK2 that lead to atypical (8/88) and variant (9/88) forms of FOP.

Recent screening studies have identified compounds that inhibit BMP signaling by ALK2. However, these compounds also inhibit kinases from multiple signaling pathways rather significantly and thus are unsuitable for clinical applications.

Thus, it would be beneficial to identify compounds or molecules that inhibit the ALK2 kinase without significantly affecting any other kinases. The present invention provides a useful method for the identification of putative inhibitors of activin-like receptor kinases that destabilize the proteins by binding at a site other than the highly conserved ATP-binding cleft or active site. The present invention is also directed to compounds identified by the methods described herein.

SUMMARY OF THE INVENTION

An embodiment of the claimed invention is directed to a method for screening a compound that binds to an allosteric site of ALK2, the method comprising screening for a compound that is capable of destabilizing the ALK2 protein. A further embodiment of the invention is directed to a pharmaceutical composition for the treatment and/or prophylaxis of a disease in a vertebrate, said composition comprising at least one ALK receptor kinase inhibitor, and optionally a pharmaceutically acceptable carrier, adjuvant and/or diluent.

DESCRIPTION OF THE INVENTION

The present invention relates to the finding that inhibitors of activin-like receptor kinases are useful therapeutics for the treatment and/or prophylaxis of certain disease conditions. These inhibitors are identified by calculating their binding affinities at a particular location of the ALK2 receptor kinase, wherein the location is not the active site of the protein.

Small molecule protein kinase inhibitors can be categorized into three classes according to their binding mode: type I, type II and type III. The majority of known kinase inhibitors fall into the type I class and compete against the ATP substrate by binding in and occluding the highly conserved adenine pocket of the enzyme active site. Unfortunately, achievement of high selectivity is usually difficult with type I inhibitors. Type II compounds bind to an extended ATP site, which includes the adenine pocket but also an additional cleft unique to the inactive conformation of the enzyme. The third class, the type III inhibitors, bind to sites other than (allosteric) the ATP-binding pocket of the enzyme, hence are non-competitive. Binding can induce conformational changes in the protein that diminish activity. Although a mere handful of type III inhibitors have been developed for the small subset of kinases that are targetable on this basis, high selectivity can be achieved. The novel allosteric inhibitors of activin-like kinases encompassed by the claimed invention, fall into this latter category.

Studies performed on the structural basis of dysregulation of the ALK2 receptor kinase by FOP-linked mutations, have revealed a novel target site for small molecule inhibitors that is adjacent to a regulatory subdomain of the enzyme.

Screening assays were set up to identify compounds that were capable of binding to a specific location in ALK2. This location was a ring-shaped pocket that contains a single centrally located sidechain, that of a histidine in ALK1 and ALK2, and an aspartate in the other five receptor kinases of the family. Numerous compounds were docked in poses that wrap the scaffolds around the central "island" residue, with terminal groups oriented in a head-to-tail fashion. Covalent linkage of the juxtaposed groups to form macrocyclic compounds is likely feasible in many cases. Through reduction in the entropic cost of binding due to constraint of rotatable bonds, as well as other properties, macrocycles have become an attractive scaffold for medicinal chemists in modern drug discovery.

According to an embodiment of the invention, there is provided a method for identifying compounds or molecules that bind to a specific location of ALK2. In certain embodiments, the location is one that is not the active site of the protein.

According to a further embodiment of the invention, a screening assay is carried out to identify compounds that bind to an allosteric site of ALK2 and cause destabilization of the protein.

Figure 1:
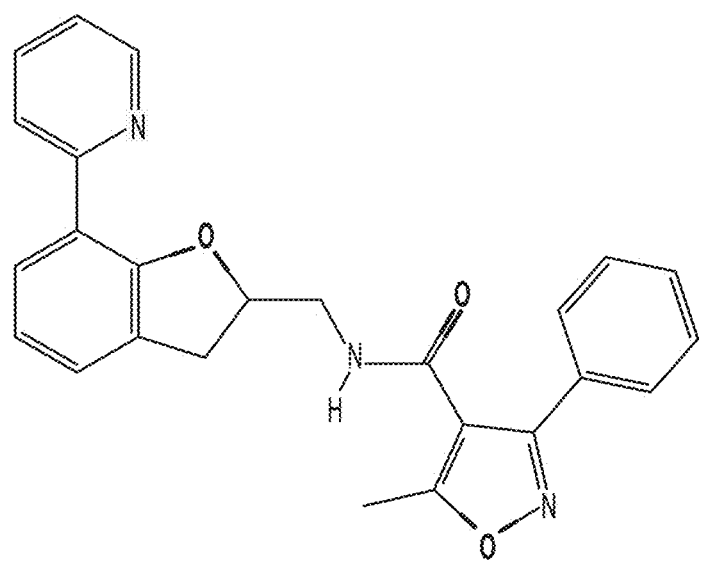
FIG. 1 shows the structure of compound 8.

In an embodiment of the invention, a compound (referred to herein as compound 8 or C8) identified by this method is 5-methyl-3-phenyl-N-{[7-(2-pyridinyl)-2,3-dihydro-1-benzofuran-2-yl]methyl}-4-isoxazolecarboxamide (FIG. 1). In other embodiments, compounds that cause destabilization of ALK-2 are benzoates (compounds 14 and 24), pyridine (compound 28), and oxadiazoles (compounds 17, 19 and 20).

Figure 2:
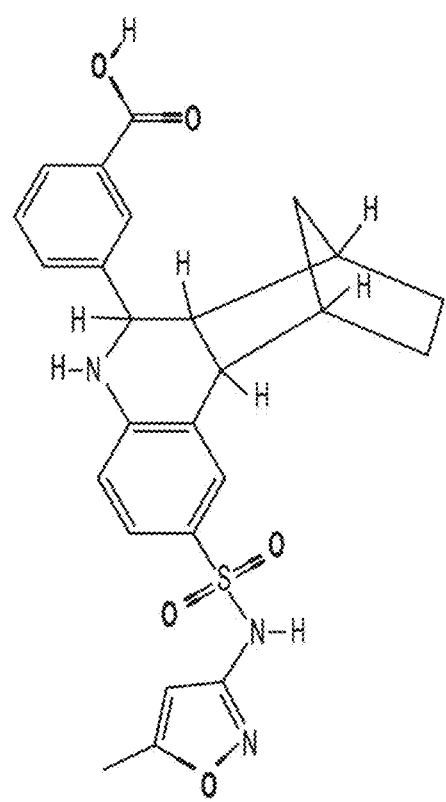
FIG. 2 shows the structure of compound 14.
Figure 3:
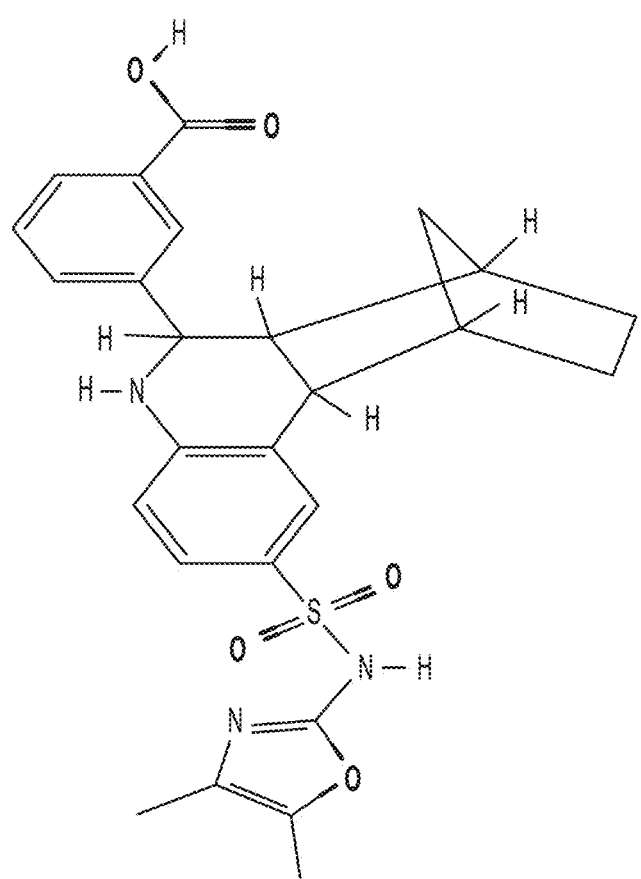
FIG. 3 shows the structure of compound 24.
Figure 4:
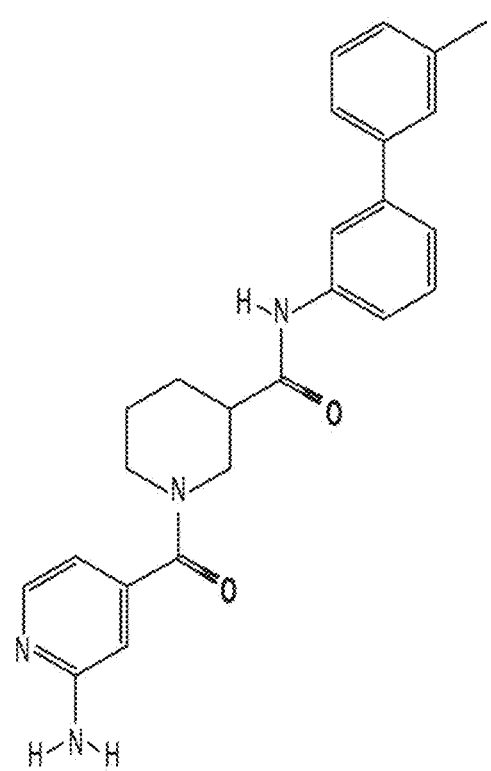
FIG. 4 shows the structure of compound 28.
Figure 5:
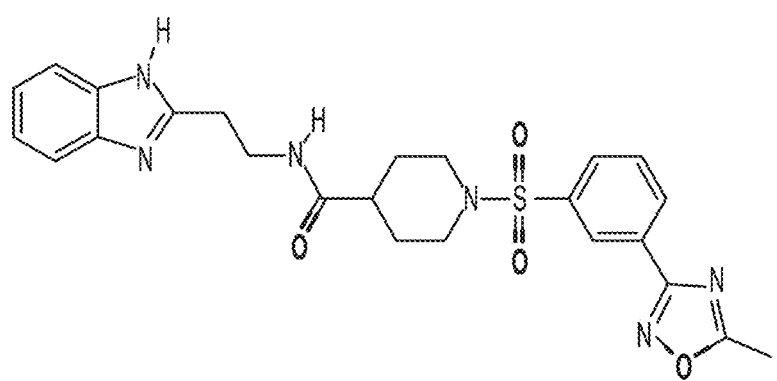
FIG. 5 shows the structure of compound 17.
Figure 6:
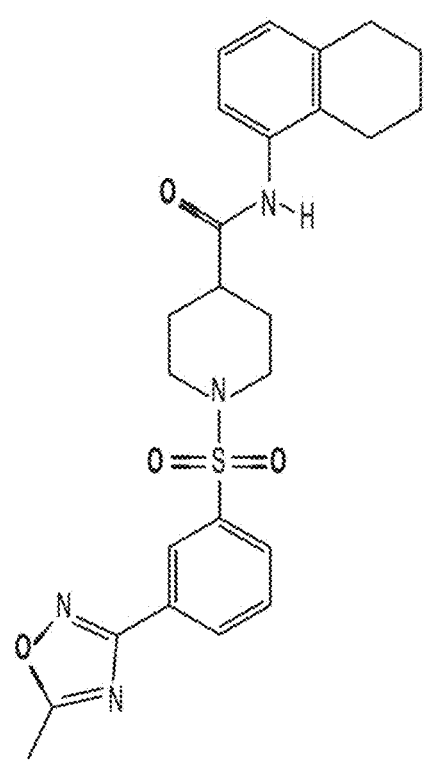
FIG. 6 shows the structure of compound 19.
Figure 7:
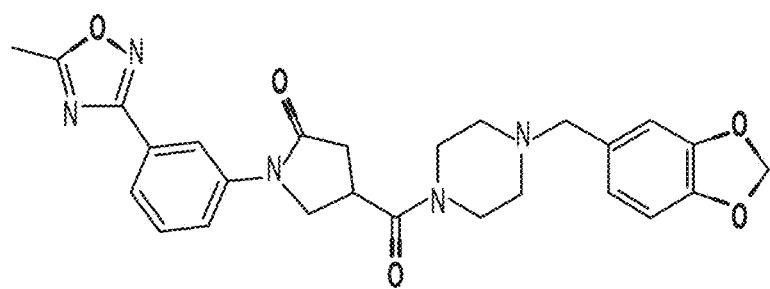
FIG. 7 shows the structure of compound 20.

Compound 14 is 3-{2-[(5-methyl-1,2-oxazol-3-yl)sulfamoyl]-5,6,6a,7,8,9,10,10a-octahydro-7,10-methanophenanthridin-6-yl}benzoic acid (FIG. 2). Compound 24 is 3-{2-[(4,5-dimethyl-1,3-oxazol-2-yl)sulfamoyl]-5,6,6a,7,8,9,10,10a-octahydro-7,10-methanophenanthridin-6-yl}benzoic acid (FIG. 3). Compound 28 is 1-(2-aminoisonicotinoyl)-N-(3'-methyl-3-biphenylyl)-3-piperidinecarboxamide (FIG. 4). Compound 17 is N-[2-(1H-1,3-benzodiazol-2-yl)ethyl]-1-[3-(5-methyl-1,2,4-oxadiazol-3-yl)benzenesulfonyl]piperidine-4-carboxamide (FIG. 5). Compound 19 is 1-[3-(5-methyl-1,2,4-oxadiazol-3-yl)benzenesulfonyl]-N-(5,6,7,8-tetrahydronaphthalen-1-yl)piperidine-4-carboxamide (FIG. 6). Compound 20 is 4-[4-(1,3-benzodioxol-5-ylmethyl)piperazine-1-carbonyl]-1-[3-(5-methyl-1,2,4-oxadiazol-3-yl)phenyl]pyrrolidin-2-one (FIG. 7).

According to an embodiment of the invention, there is provided a pharmaceutical composition for the treatment and/or prophylaxis of disease associated with an ALK2 mutation, said composition comprising at least one ALK2 inhibitor, and optionally a pharmaceutically acceptable carrier, adjuvant and/or diluent.

According to another embodiment of the invention, there is provided a process for preparing a pharmaceutical composition as defined in the first embodiment of the invention, wherein said process comprises homogeneously mixing at least one ALK2 inhibitor with a pharmaceutically acceptable carrier, adjuvant and/or diluent.

Typically, the vertebrate is selected from the group consisting of human, non-human primate, mice, cattle, sheep, goats, horses, rabbits, birds, cats and dogs. More typically, the vertebrate is human, non-human primate or mouse. Even more typically, the vertebrate is human.

According to another embodiment of the invention, there is provided a method for the treatment of disease associated with an ALK2 mutation in a vertebrate in need of said treatment, wherein said method comprises administering to said vertebrate, a therapeutically effective amount of at least one ALK2 inhibitor.

According to certain embodiments, the disease associated with the ALK2 mutation is FOP. In other embodiments, the disease is a cancer.

In an embodiment of the invention, a test compound identified by the methods of the claimed invention was found to significantly destabilize the ALK2 kinase through the formation of hydrogen bonds, as evidenced by SDS-PAGE analyses (FIG. 8) and thermostability assays.

In essence, the compound behaved similar to "suicide" inhibitors that irreversibly block the activity of enzymes through formation of unresolvable covalent intermediates. Because the underlying premise of the screen was to identify compounds that would act like "molecular putty", binding adjacent to and stabilizing the autoinhibitory GS subdomain, de-stabilization would also be anticipated, as in the case of the test compound.

In a test compound identified by the methods of the claimed invention, the isoxazole ring of compound 8 is docked adjacent to a residue (Arg258) that plays a key role in stabilizing the GS subdomain and may act as a trigger which could be targeted through the design of other compounds. Suicide-like inhibitors that eliminate active protein would likely possess superior pharmokinetic properties relative to steady-state binding drugs that are cleared from circulation and require frequent administration. Since BMP signals are propagated during endocytic trafficking, rather than from the plasma membrane, reducing levels of active protein in endosomes might prove to be an especially effective mechanism of inhibition in vivo.

In addition to the guanidino group of Arg258 that mediates the destabilizing effects of the inhibitor, another functional group of great import, the sidechain thiol of Cys351, may also interact with bound compounds. In this case, rather than formation of a hydrogen bond, a covalent linkage is formed. Covalently linked inhibitors have irreversible effects and are often referred to as suicide, compared to competitive, inhibitors. With the highly reactive sidechain thiol lying just at the surface of a sub-pocket of the binding site, the allosteric inhibitors targeting the site permit irreversible, covalent linkages to form. The putative covalently liked inhibitors act through the same mechanism as the noncovalent counterparts, but rather than binding through the typical complement of interactions and driving forces, they become irreversibly linked. In sum, covalently linked and noncovalently-linked inhibitors exhibit the same mechanism of effect, but do so through distinct binding modes.

Working Examples

Destabilizing effects of a compound identified by a method of the claimed invention, were observed by SDS and native polyacrylamide gel electrophoresis analyses (FIG. 8), and were confirmed by monitoring protein unfolding with a hydrophobic fluoroprobe (SYPRO orange) in 96-well plate format with a quantitative PCR instrument (Thermofluor assay). The allosteric inhibitor shifted the melting temperature of Dorsomorphin-stabilized ALK2 from approximately 55° C. down to 35° C. in a concentration dependent manner that correlated with concentration dependent inhibition of ALK2 kinase activity.

Figure 8:
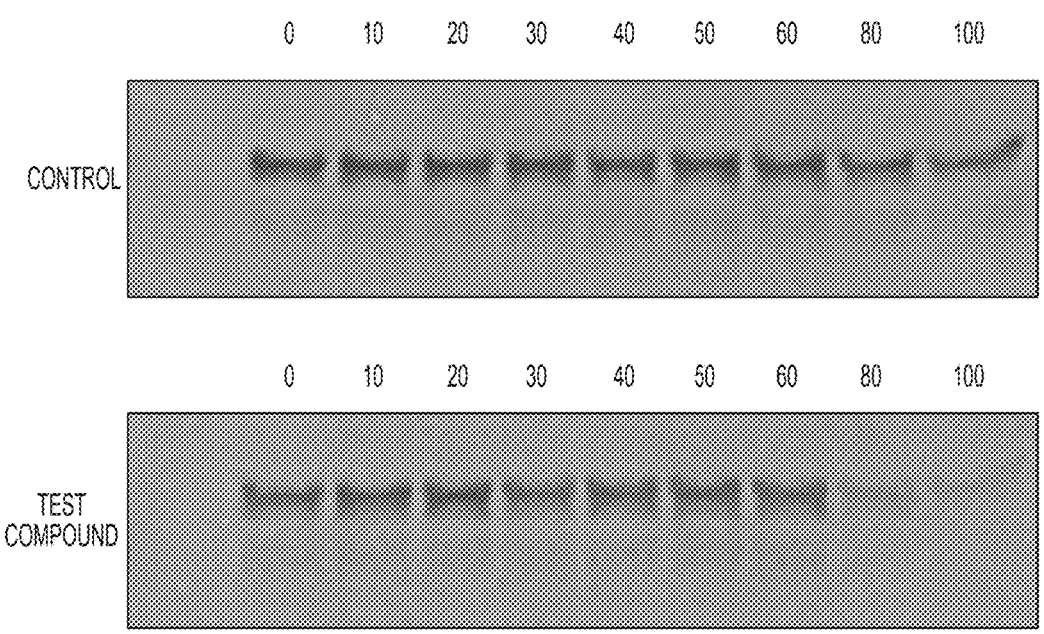
FIG. 8 shows the destabilization of ALK2 receptor kinase by compound 8.

As shown in FIG. 8, the top panel shows the protein analyzed by gel electrophoresis analysis in the presence of a control compound. The bottom panel in FIG. 8 shows the protein incubated with increasing concentrations of a test compound (allosteric inhibitor) and destabilization of the protein at higher concentrations of the test compound relative to the control.

Figure 9:
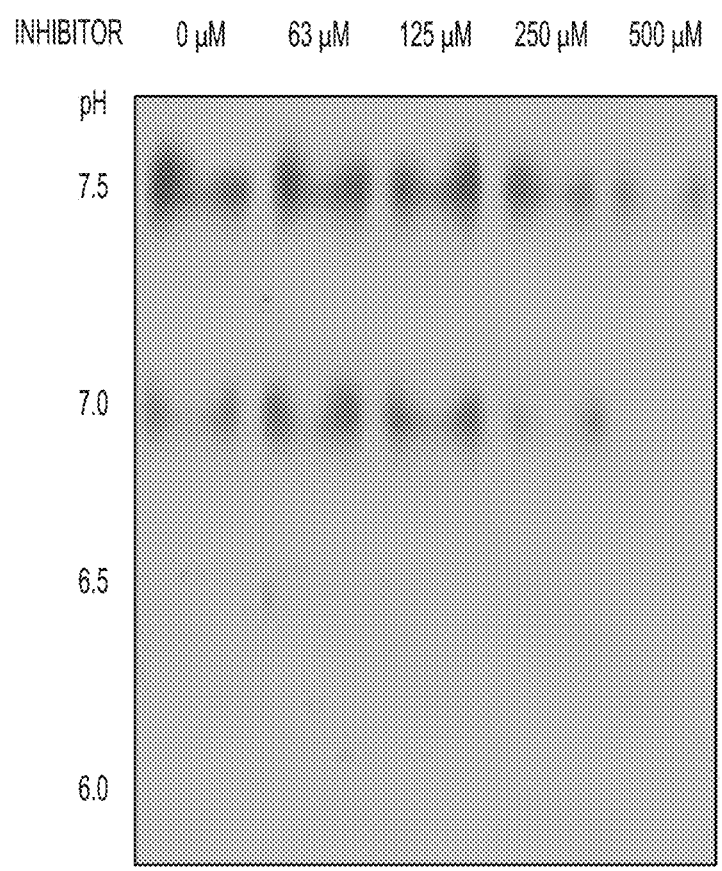
FIG. 9 shows the effect of decreasing pH on the kinase protein.
Figure 10:
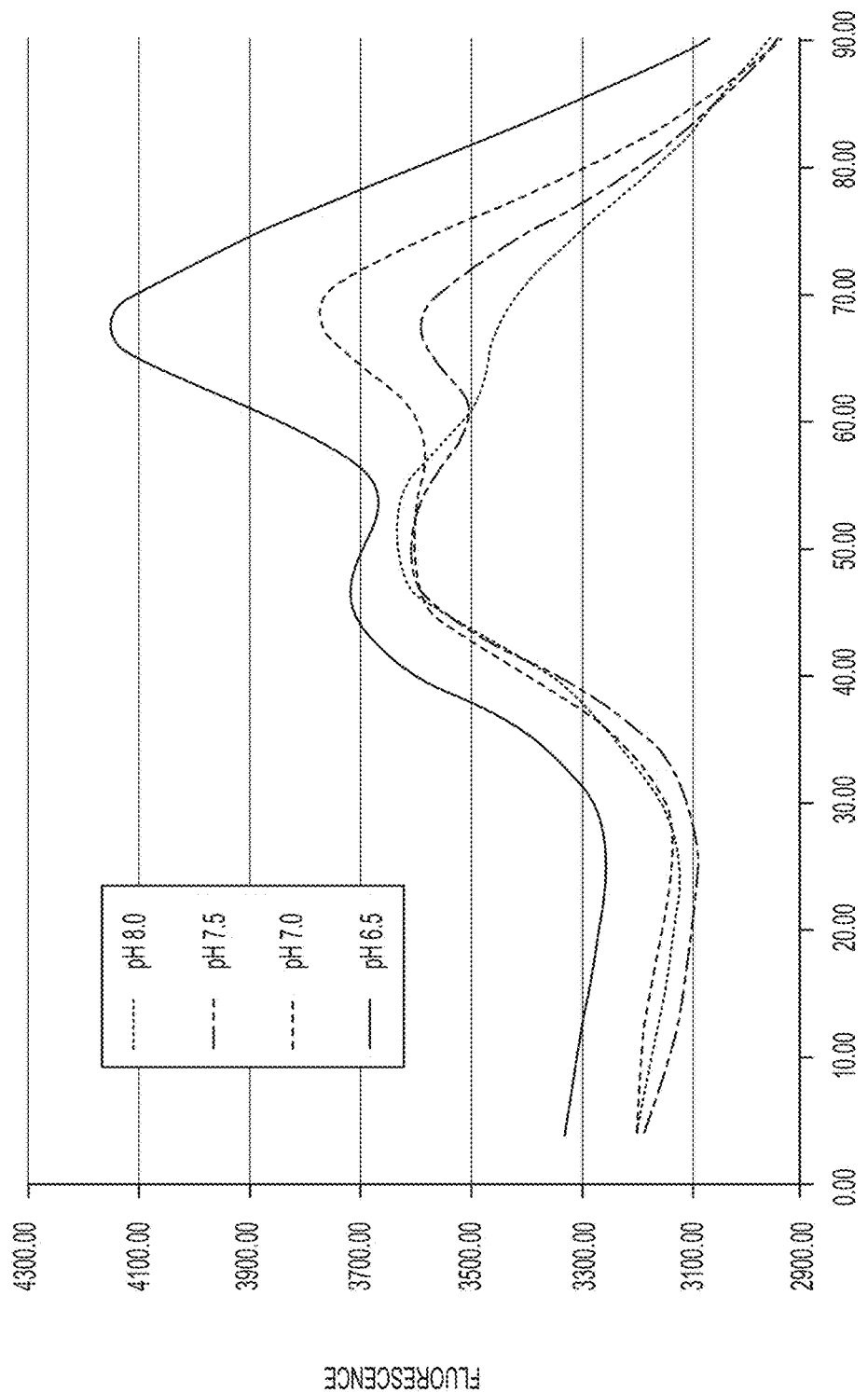
FIG. 10 shows the effect of decreasing pH on the stability of the kinase protein.
Figure 11:
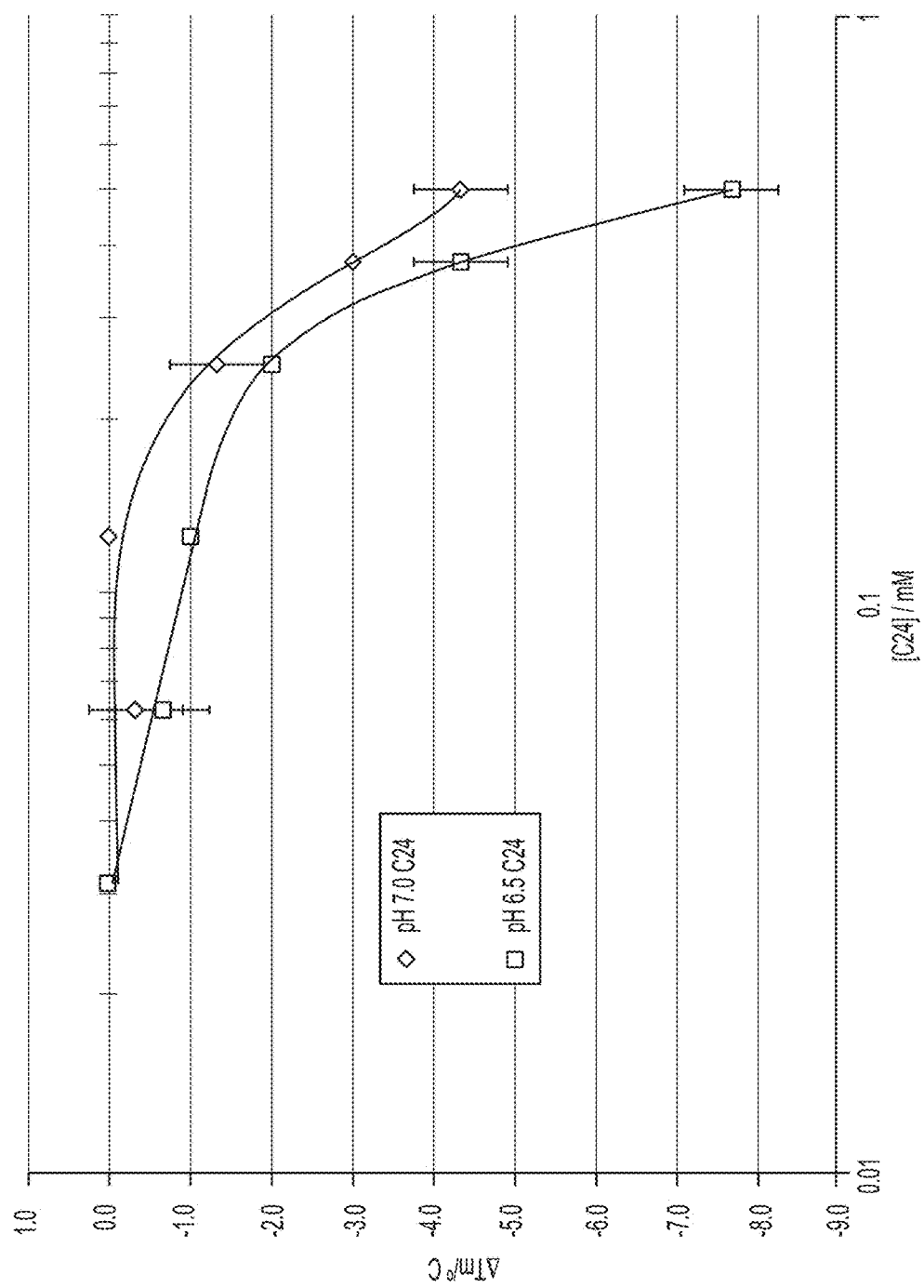
FIG. 11 shows the effect of decreasing pH on the sensitivity of the kinase protein to an allosteric destabilizer.

The comparative stabilities of the kinase protein were tested at varying pH levels in the presence of compounds identified by the methods of the claimed invention. As shown by native polyacrylamide gel electrophoresis in FIG. 9, with decreasing pH, the kinase protein becomes inherently less stable, hence increasingly more sensitive to further destabilization by an allosteric destabilizer. Thermofluor assays provide independent confirmation of the effect of decreasing pH on the stability (FIG. 10) and sensitivity to an allosteric destabilizer (FIG. 11) of the kinase protein. Therefore, derivatives that enter into clinical trials could be dosed at concentrations that do not destabilize the kinase protein under normoxic conditions, but do under hypoxic because of the increased efficacy at lower intracellular pH. Hypoxic conditions typically occur in tissues that are faced with traumas such as those caused by surgery or injury.

In addition to the efficacy of an allosteric destabilizer in hypoxic tissue, a second major advantage stems from such a selective inhibitor of a BMP receptor kinase. Recently, BMP signaling has been shown to be the principle pathway controlling muscle mass, dominating the effects of myostatin, which signals through the Smad2/3 rather than the Smad1/5/8 pathway. Indeed, pharmacological inhibition of BMP signaling with a derivative of the ATP-competitive inhibitor dorsomorphin (LDN-193189) leads to muscle wasting or cachexia. Hence long-term treatment with an ATP-competitive inhibitor, no matter how specific, would likely lead to skeletal muscle wasting. Too low a dose could lead to heterotopic bone formation, too high to cachexia. Thus skeletal muscle would either be mineralized or lost. In contrast, an allosteric destabilizer that selectively leads to degradation of the kinase in hypoxic tissue following trauma or surgery could potentially be dosed to prevent both highly undesirable consequences.

The implications for such a finding are that an allosteric destabilizer compound could be taken prophylactically, one that is already unique by (1) binding at another site, not inhibiting activity by competing with ATP and by (2) destabilizing/unfolding the protein to be degraded by the proteasome at a low basal level, then would only become efficacious in soft tissues upon trauma.

Those having skill in the art, with the knowledge gained from the present disclosure, will recognize that various changes could be made to the methods disclosed herein without departing from the scope of the present invention. Mechanisms used to explain theoretical or observed phenomena or results, shall be interpreted as illustrative only and not limiting in any way the scope of the appended claims.

What is claimed is:

1. A pharmaceutical composition for the treatment and/or prophylaxis of a disease in a vertebrate, said composition comprising at least one activin-like receptor kinase (ALK) inhibitor, and optionally a pharmaceutically acceptable carrier, adjuvant and/or diluent, wherein the ALK inhibitor is selected from the group consisting of 5-methyl-3-phenyl-N-{[7-(2-pyridinyl)-2,3-dihydro-1-benzofuran-2-yl] methyl}-4-isoxazolecarboxamide, 3-{2-[(5-methyl-1,2-oxazol-3-yl)sulfamoyl]-5,6,6a,7,8,9,10,10a-octahydro-7,10-methanophenanthridin-6-yl}benzoic acid, 3-{2-[(4,5-dimethyl-1,3-oxazol-2-yl)sulfamoyl]-5,6,6a,7,8,9,10,10a-octahydro-7,10-methanophenanthridin-6-yl}benzoic acid, 1-(2-aminoisonicotinoyl)-N-(3'-methyl-3-biphenylyl)-3-piperidinecarboxamide, N-[2-(1H-1,3-benzodiazol-2-yl)ethyl]-1-[3-(5-methyl-1,2,4-oxadiazol-3-yl)benzenesulfonyl]piperidine-4-carboxamide, 1-[3-(5-methyl-1,2,4-oxadiazol-3-yl)benzenesulfonyl]-N-(5,6,7,8-tetrahydronaphthalen-1-yl)piperidine-4-carboxamide, and 4-[4-(1,3-benzodioxol-5-ylmethyl)piperazine-1-carbonyl]-1-[3-(5-methyl-1,2,4-oxadiazol-3-yl)phenyl]pyrrolidin-2-one.

2. The pharmaceutical composition of claim 1, wherein the ALK inhibitor binds to an allosteric site on the ALK receptor kinase.

3. The pharmaceutical composition of claim 1, wherein the ALK inhibitor is selected from the group consisting of isoxazoles, benzoates, pyridines and oxadiazoles.

4. The pharmaceutical composition of claim 1, wherein the inhibitor is 5-methyl-3-phenyl-N-{[7-(2-pyridinyl)-2,3-dihydro-1-benzofuran-2-yl] methyl}-4-isoxazolecarboxamide.

5. The pharmaceutical composition of claim 2, wherein the ALK inhibitor interacts with a guanidino group on an arginine residue in the allosteric site of ALK-2.

6. The pharmaceutical composition of claim 5, wherein the arginine residue is Arg258.

7. The pharmaceutical composition of claim 1, wherein the disease is FOP.

8. The pharmaceutical composition of claim 1, wherein the disease is a cancer.

* * * * *